United States Patent [19]
Kaltman et al.

[11] Patent Number: 5,711,026
[45] Date of Patent: Jan. 27, 1998

[54] DISPOSABLE NOSE PROTECTOR ASSEMBLY

[75] Inventors: Martin Kaltman, Old Westbury; Joel A. Weingold, South Bellmore; William Plumb, New York, all of N.Y.

[73] Assignee: Queens Group, Inc., Long Island City, N.Y.

[21] Appl. No.: 568,415

[22] Filed: Dec. 6, 1995

[51] Int. Cl.$^6$ .................................................. A41D 13/00
[52] U.S. Cl. ............................... 2/9; 2/206; 128/858
[58] Field of Search .................... 2/206, 9, 174, 2/455, 15, 11; 602/54, 57, 74, 58; 128/857, 858, 887, 888; 604/307; 428/40.1, 41.7, 41.8

[56] References Cited

U.S. PATENT DOCUMENTS

| | | | |
|---|---|---|---|
| 1,048,191 | 12/1912 | Maurice | 2/206 |
| 1,354,652 | 10/1920 | Jefferies | 128/857 |
| 1,436,313 | 11/1922 | Hafer | 2/206 |
| 1,761,664 | 6/1930 | Harris | 2/206 |
| 2,233,698 | 3/1941 | Girouard | 2/206 |
| 2,364,354 | 12/1944 | Felch | 2/206 |
| 2,519,561 | 8/1950 | Gillman | 2/206 |
| 3,068,863 | 12/1962 | Bowman | 128/858 |
| 3,092,103 | 6/1963 | Mower | 128/858 |
| 3,594,813 | 7/1971 | Sanderson | 2/2 |
| 3,691,140 | 9/1972 | Silver | 526/240 |
| 3,695,265 | 10/1972 | Brevik | 128/206.14 |
| 4,534,342 | 8/1985 | Paxa | 602/74 |
| 4,674,133 | 6/1987 | Oschner | 2/206 |
| 4,701,962 | 10/1987 | Simon | 128/858 |
| 4,719,909 | 1/1988 | Micchia et al. | 128/858 |
| 4,745,916 | 5/1988 | Seber | 128/858 |
| 4,944,040 | 7/1990 | Riedel et al. | 128/858 |
| 5,167,036 | 12/1992 | Daprato | 2/9 |
| 5,191,897 | 3/1993 | Meshel | 128/858 |
| 5,274,847 | 1/1994 | Lauttamus | 2/9 |
| 5,592,687 | 1/1997 | Lajeunesse | 2/9 |

*Primary Examiner*—Amy B. Vanatta
*Attorney, Agent, or Firm*—Ostrolenk, Faber, Gerb & Soffen, LLP

[57] ABSTRACT

A pad or roll comprising a plurality of separable disposable flexible sheets, each sheet optionally having a detachable portion, the sheets or detachable portions thereof being capable of blocking solar ultraviolet radiation, each such sheet or detachable portion thereof having two symmetrically positioned opposed edges and a configuration conformable to the surface of a person's nose, each sheet or detachable portion thereof having a front surface and a rear surface, the rear surface being provided with nontoxic adhesive means for releasably adhering the sheet or detachable portion thereof to a person's nose.

3 Claims, 7 Drawing Sheets

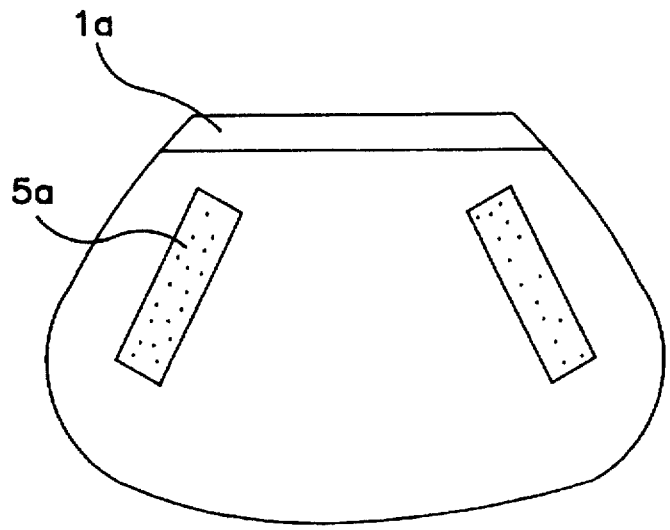
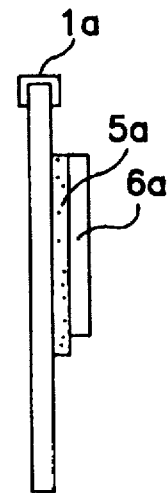
FIG. 3a  FIG. 3b
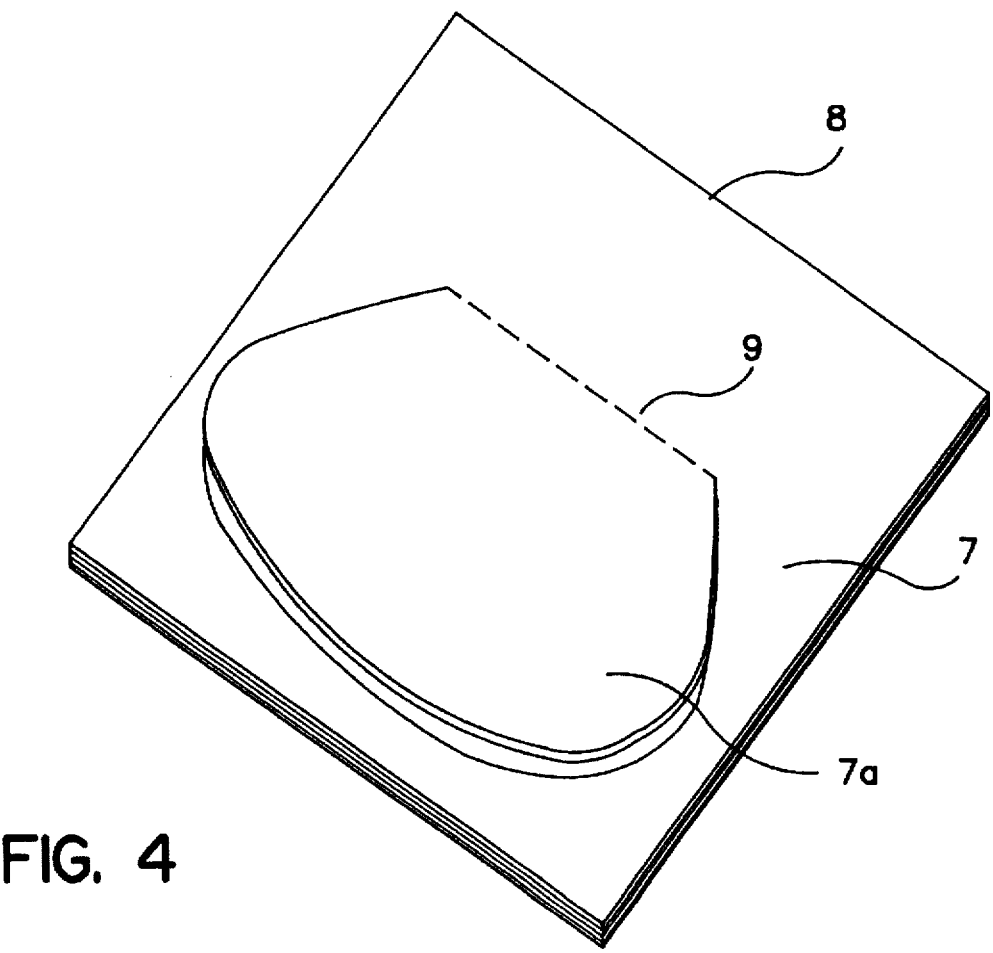
FIG. 4

DISPOSABLE NOSE PROTECTOR ASSEMBLY

BACKGROUND OF THE INVENTION

The present invention relates to nose protector assemblies. A nose protector as herein described is a device fitting over a person's nose to protect it from harmful solar ultraviolet radiation. Such devices are known in the art in the form of individual nose protectors.

SUMMARY OF THE INVENTION

It is an object of the present invention to provide a convenient and economical assembly for dispensing disposable nose protectors.

The invention provides such assemblies in the form of pads or rolls, each comprising a plurality of disposable flexible sheets. Each sheet is or optionally has a detachable nose protector portion which is capable of blocking solar ultraviolet radiation. Each nose protector has two symmetrically positioned opposed edges and a configuration, preferably generally trapezoidal, conformable to the surface of a person's nose. The rear surface of each nose protector is provided with non-toxic adhesive means for releasably adhering the nose protector to a person's nose. The non-toxic adhesive means may be a coating of non-toxic pressure sensitive adhesive over at least a portion of the rear surface, or may comprise strips adhered to the rear surface of the nose protector, the outer surface of each strip being coated with a pressure sensitive adhesive, which may be covered with a removable protective strip.

The nose protector assembly may be in the form of a pad comprising a plurality of disposable flexible sheets, the coating of pressure sensitive adhesive being provided in striplike positions adjacent to each of the symmetrically positioned opposing edges of the sheets and serving to releasably adhere each sheet to an underlying sheet, thereby forming a pad.

The nose protector assembly may also be in the form of a plurality of backing sheets, each of which has a disposable nose protector in the form of a flexible sheet capable of blocking solar ultraviolet radiation releasably adhered thereto by pressure sensitive, nontoxic adhesive disposed on one surface to the flexible sheet, which adhesive is capable of releasably adhering to the human skin.

When in the form of a roll, the assembly of the invention is provided with spaced apart rows of perforations whereby separable sheets may be separated from the roll.

The flexible material of the nose protector is preferably paper.

Other features and advantages of the present invention will become apparent from the following description of the invention which refers to the accompanying drawings.

BRIEF DESCRIPTION OF THE DRAWINGS

FIG. 3a and 3b are rear and side views, respectively, of a pad according to another embodiment of the present invention.

FIG. 4 is an orthographic view of still another embodiment of the invention.

DETAILED DESCRIPTION OF THE PREFERRED EMBODIMENTS

The present invention can be provided in a number of different embodiments. The preferred embodiments of the invention are described in the following examples.

EXAMPLE 1

Figure 1:
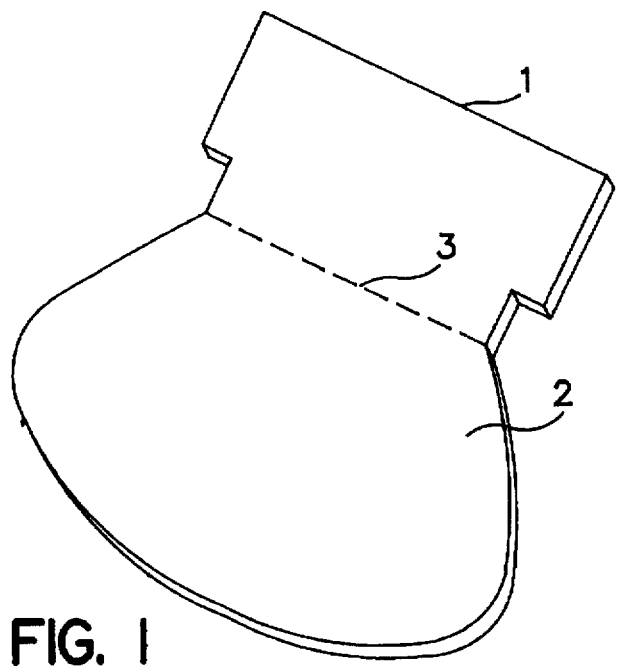
FIGS. 1, 2a and 2b are front, rear and side views, respectively, of a pad according to one embodiment of the present invention.
Figure 2:
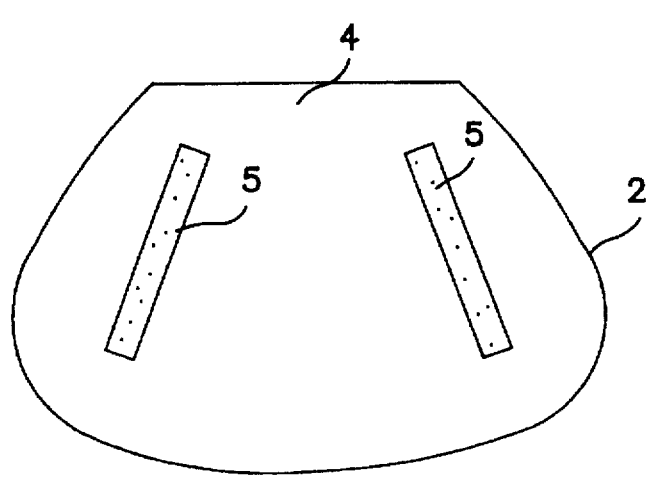
Figure 2B:
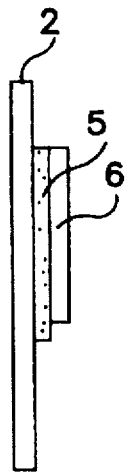

FIGS. 1, 2a and 2b illustrate a first embodiment of the invention. In this embodiment, as shown in FIG. 1, a pad is fastened at its upper end 1 and comprises sheets 2 detachable at perforations 3. The detachable sheets 2 are provided in a configuration conforming to the surface of a person's nose and are referred to herein as nose protectors. As shown in FIG. 2a, each sheet is provided on its rear surface 4 with adhesive strips 5, the adhesive of the strip being a non-toxic pressure sensitive type. The adhesive surfaces of strips 5 may be covered with removable, protective strips 6, as shown in FIG. 2b.

EXAMPLE 2

FIGS. 3a and 3b illustrate a variation of the embodiment of Example 1, wherein the pad, fastened at its upper end by binding strip 1a, consists of sheets configured to conform to a person's nose. The sheets are provided on their rear surfaces with adhesive strips 5a and removable protective strips 6a, as in Example 1.

EXAMPLE 3

FIG. 4 illustrates another embodiment of the invention in which the pad comprises sheets 7 fastened at their upper end 8 and having nose protector portions 8, detachable from said sheets at perforations 9. The detachable portions 7a are configured similarly to sheets 2 in FIG. 1 and are similarly provided with adhesive strips on their rear surfaces.

EXAMPLE 4

Figure 5:
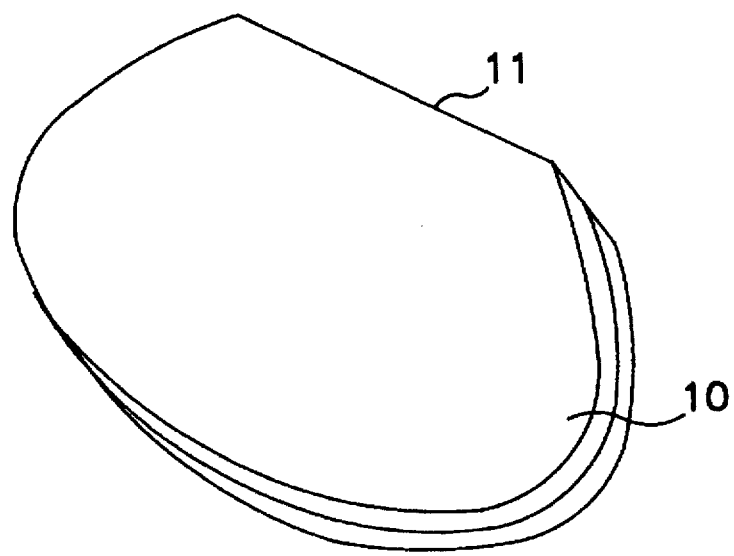
FIGS. 5 and 6 are front and rear views, respectively, of a pad according to still another embodiment of the present invention.
Figure 6:
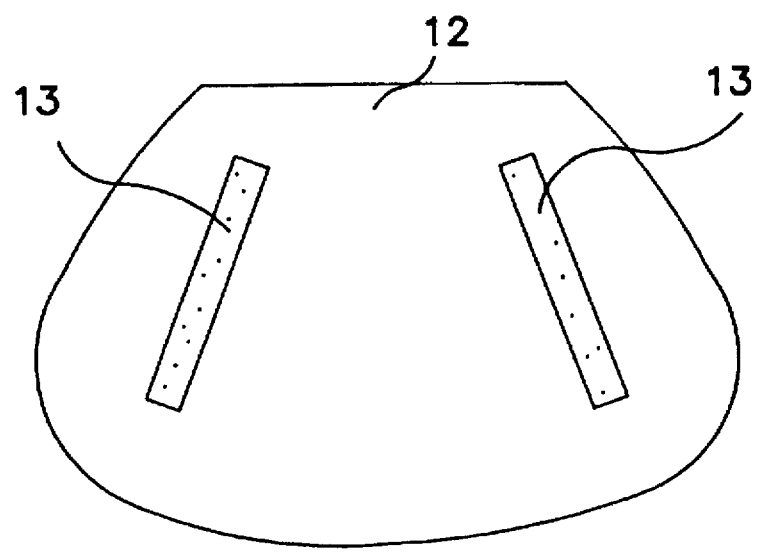

FIGS. 5 and 6 illustrate an embodiment in which the pad consists of sheets 10 having a configuration conforming to the surface of a person's nose, the sheets being fastened at their upper ends 11. The backing sheets 14 are free of adhesive. The rear surface 12 of each sheet 10 is provided with a releasable pressure sensitive adhesive coating 13. Each sheet, except for the bottom sheet, is releasably adhered to the front of another sheet, forming a pad in the manner of "Post It" notes.

EXAMPLE 5

Figure 7:
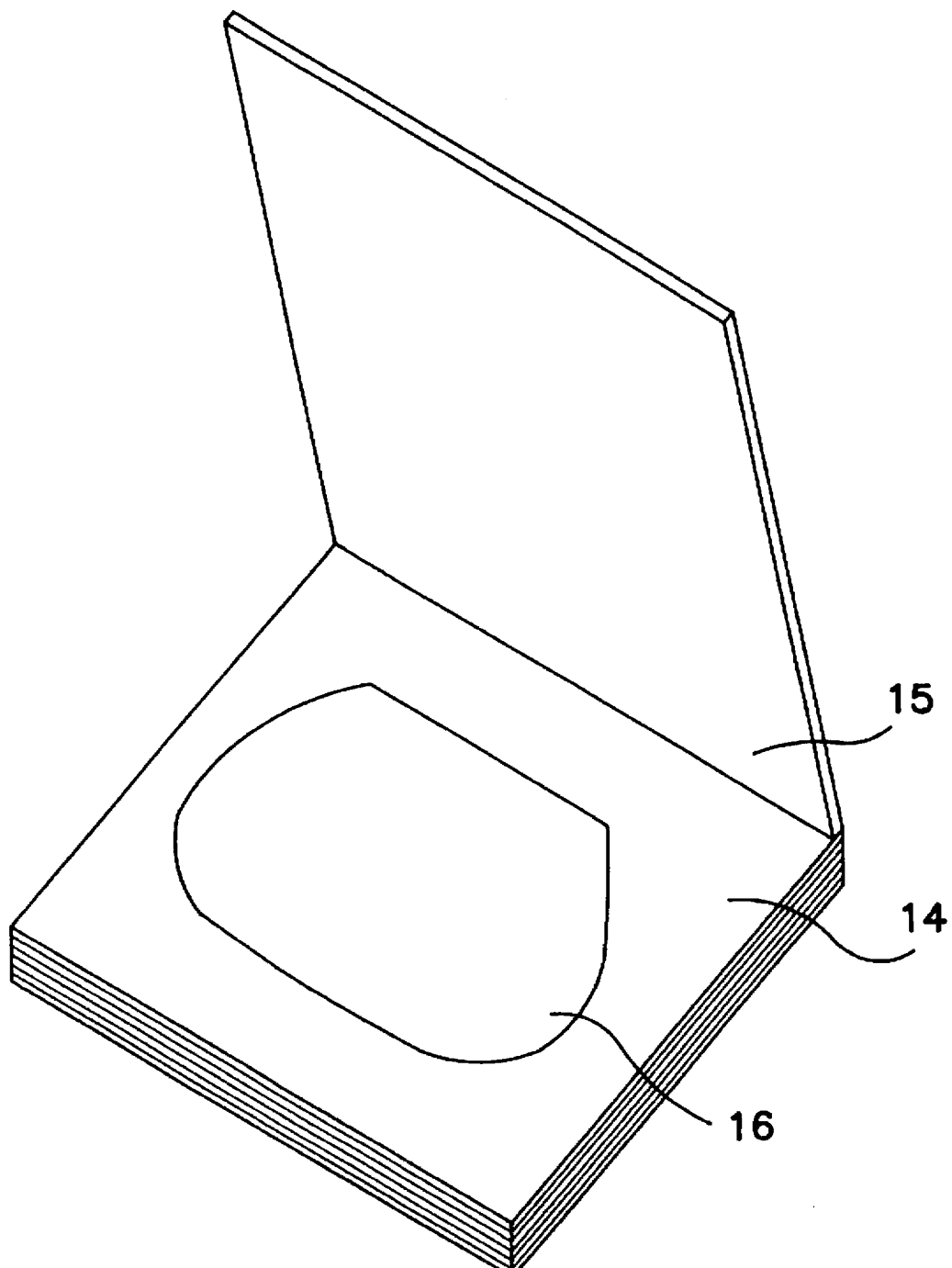
FIG. 7 is an orthographic view of yet another embodiment of this invention.
Figure 8:
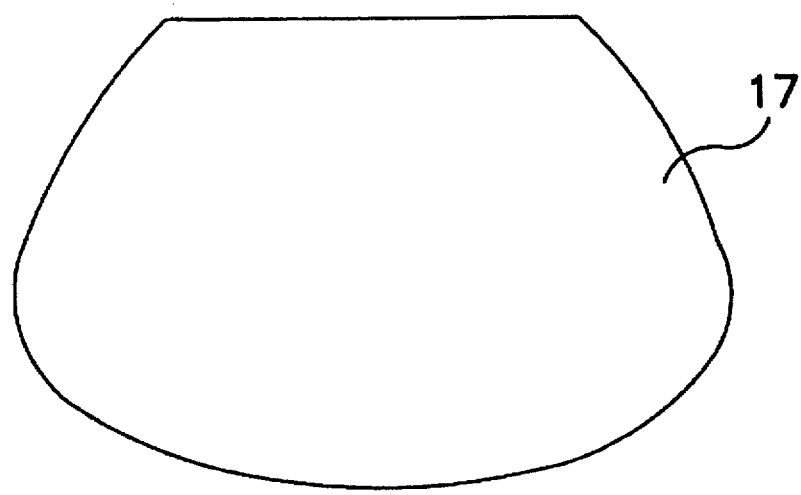
FIGS. 8 and 9 are front and rear views, respectively, of a further embodiment of the present invention.
Figure 9:
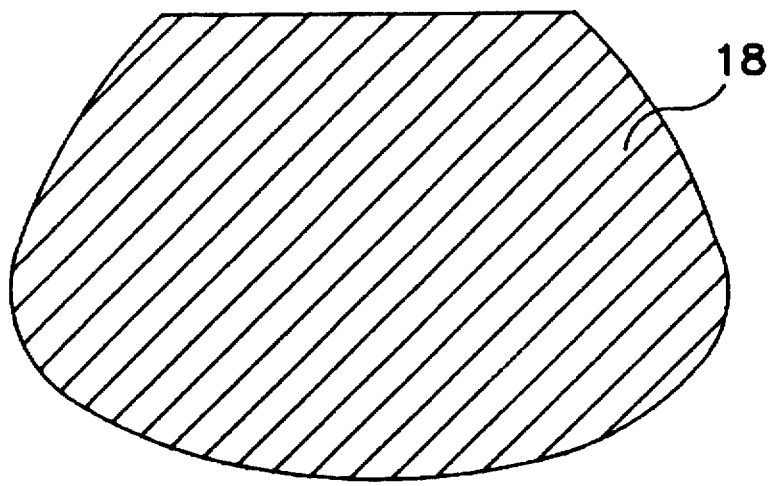

FIG. 7 illustrates an embodiment comprising a pad of backing sheets 14 fastened at its upper end 15 and removable sheets 16 having a configuration conforming to the surface of a person's nose. Sheets 16 are coated on their rear surfaces with a releasable pressure sensitive adhesive for releasably adhering them to the backing sheets 14. FIGS. 8 and 9 show the front 17 and back 18 of an individual sheet of this type, the adhesive layer being shown by the hatching on the back surface.

EXAMPLE 6

Figure 10:
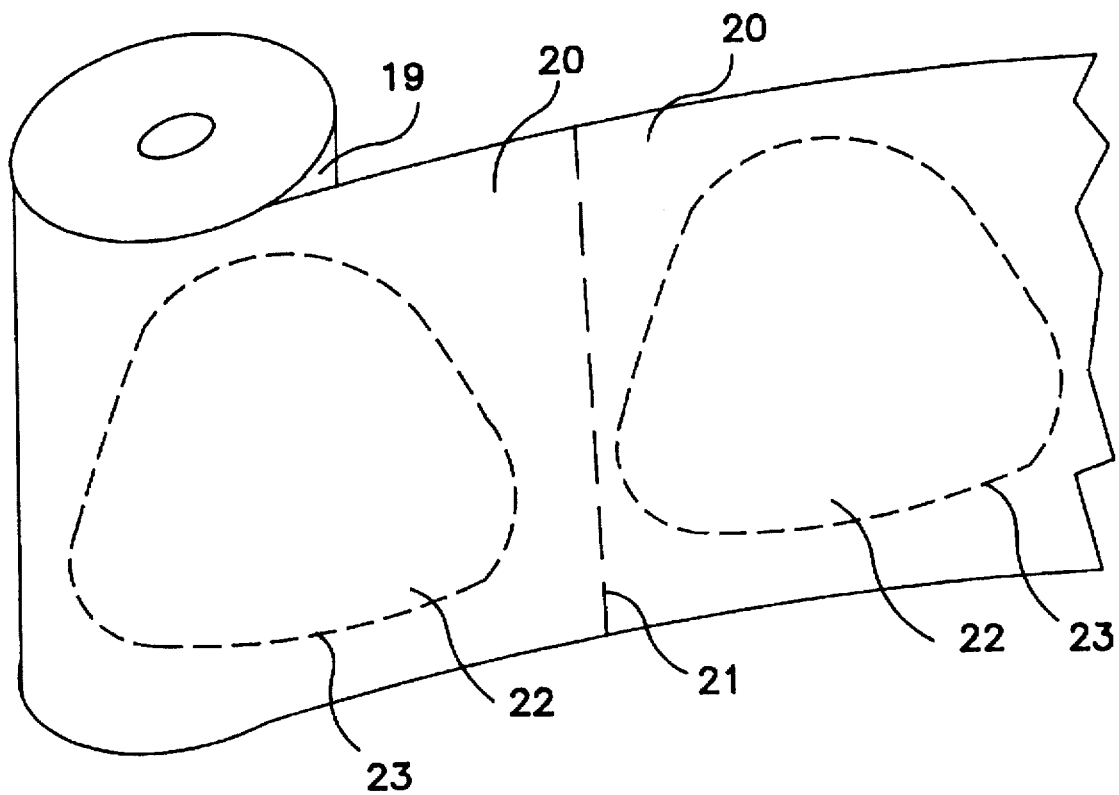
FIG. 10 is an orthographic projection of a still further embodiment of the present invention in the form of a roll.

FIG. 10 illustrates an embodiment in the form of a roll 19 having sheets 20 detachable at perforations 21. Each sheet includes a further detachable portion 22 bounded by perforations 23. Portions 22 have configurations conforming to the surface of a person's nose and are provided with an adhesive layer on their rear surfaces as in FIG. 9.

Figure 11:
FIG. 11 illustrates the nose protector of the present invention applied to a person's nose.

FIG. 11 shows a nose protector 23 of this invention applied to a person's nose.

As shown the nose protector is applied longitudinally with respect to the symmetrically positioned opposed edges and covers the entire nose.

Although the present invention has been described in relation to particular embodiments thereof, many other variations and modifications and other uses will become apparent to those skilled in the art. The present invention is to be limited not by the specific disclosure herein, but only by the appended claims.

What is claimed is:

1. A pad comprising a plurality of backing sheets, each backing sheet being free of adhesive and having a disposable flexible sheet capable of blocking solar ultraviolet radiation releasably adhered thereto by pressure sensitive adhesive disposed on one surface of said flexible sheet, each said flexible sheet having symmetrically positioned opposing edges and a configuration conformable to the surface of a person's nose, and having a longitudinal dimension with respect to said symmetrically positioned opposed edges, sufficient to cover the entire nose, said adhesive being non-toxic and capable of releasably adhering to the human skin.

2. A pad as recited in claim 1, wherein the material of said flexible sheets is paper.

3. A pad as recited in claim 1, wherein said configuration is generally trapezoidal.

* * * * *